United States Patent [19]
Battist et al.

[11] Patent Number: 5,518,551
[45] Date of Patent: * May 21, 1996

[54] SPHEROIDAL CRYSTAL SUGAR AND METHOD OF MAKING

[75] Inventors: Gerald E. Battist; Garry L. Myers; Richard C. Fuisz, Great Falls, all of Va.

[73] Assignee: Fuisz Technologies Ltd., Chantilly, Va.

[*] Notice: The portion of the term of this patent subsequent to Oct. 7, 2013, has been disclaimed.

[21] Appl. No.: 119,974

[22] Filed: Sep. 10, 1993

[51] Int. Cl.$^6$ ..................................................... C13F 1/02
[52] U.S. Cl. ............................................................ 127/58
[58] Field of Search ................................................ 127/58

[56] References Cited

U.S. PATENT DOCUMENTS

| | | | |
|---|---|---|---|
| 2,826,169 | 3/1958 | Le Veen | 119/1 |
| 2,918,404 | 12/1959 | Mende et al. | 167/58 |
| 3,019,745 | 2/1962 | Du Bois et al. | 107/8 |
| 3,036,532 | 5/1962 | Bowe | 107/8 |
| 3,067,743 | 12/1962 | Merton et al. | 128/70 |
| 3,070,045 | 12/1962 | Bowe | 107/8 |
| 3,073,262 | 1/1963 | Bowe | 107/8 |
| 3,095,258 | 6/1963 | Scott | 18/54 |
| 3,131,428 | 5/1964 | Mika | 18/8 |
| 3,308,221 | 3/1967 | Opfell | 264/174 |

(List continued on next page.)

FOREIGN PATENT DOCUMENTS

| | | | |
|---|---|---|---|
| 609137 | 4/1988 | Australia | A61K 9/00 |
| 609135 | 4/1988 | Australia | A61K 7/48 |
| 900605 | 11/1977 | Belgium . | |
| 1303511 | 4/1988 | Canada | A61K 7/42 |
| 0287488A1 | 3/1988 | European Pat. Off. | A61K 9/20 |

(List continued on next page.)

OTHER PUBLICATIONS

R. H. Doremus, "Crystallization of Sucrose from Aqueous Solution," *Journal of Colloid and Interface Science*, 104, pp. 114–120 (1985). month not available.

P. Bennema, "Surface Diffusion and the Growth of Sucrose Crystals," *Journal of Crystal Growth*, 3,4 pp. 331–334 (1968). month not available.

T. D. Simpson, et al., "Crystalline Forms of Lactose Produced in Acidic Alcoholic Media," *Journal of Food Science*, 47, pp. 1948–1954 (1982). month not available.

A. D. Randolph, et al., "Continuous Sucrose Nucleation", *The International Sugar Journal*, pp. 8–12 (1974). month not available.

K. B. Domovs, et al., "Methanol–Soluble Complexes of Lactose and of other Carbohydrates," *J. Dairy Science*, 43, pp. 1216–1223 (1960). month not available.

A. D. Randolph, et al., "Continuous Sucrose Nucleation", *The International Sugar Journal*, pp. 35–37 (1974). month not available.

G. Arceneaux, "Flowering of Sugar Cane in Egypt," *The International Sugar Journal*, pp. 38–39 (1974). month not available.

A. D. Randolph, et al., "Continuous Sucrose Nucleation", *The International Sugar Journal*, pp. 73–77 (1974). month not available.

ICI Americas Inc., "ICI Americas Products for Cosmetics and Pharmaceuticals", (1977). month not available.

Domino Sugar Corporation, "Co–crystallization,". (1992?). month not available.

Domino Sugar Corporation, "Raspberry". (1992). month not available.

Domino Sugar Corporation, "Molasses Dark". (1992). month not available.

*Primary Examiner*—Sharon Gibson
*Assistant Examiner*—Patricia L. Hailey
*Attorney, Agent, or Firm*—Hoffmann & Baron

[57] ABSTRACT

The present invention is a new spheroidal polycrystallite product and a process for making the same. In the present invention amorphous sugar is transformed to crystalline sugar by hydrating rather than dehydrating sugar. The product of the present invention is unique in shape, size, and possesses a high degree of uniformity.

24 Claims, 4 Drawing Sheets

U.S. PATENT DOCUMENTS

| | | | |
|---|---|---|---|
| 3,324,061 | 6/1967 | Tanquary et al. | 260/29.2 |
| 3,482,998 | 12/1969 | Carroll et al. | 99/108 |
| 3,523,889 | 8/1970 | Eis | 210/20 |
| 3,557,717 | 1/1971 | Chivers | 107/54 |
| 3,595,675 | 7/1971 | Ash et al. | 99/130 |
| 3,615,671 | 10/1971 | Schoaf | 99/78 |
| 3,625,214 | 12/1971 | Higuchi | 128/260 |
| 3,676,148 | 7/1972 | De Weese et al. | 99/1 |
| 3,723,134 | 3/1973 | Chivers | 99/134 |
| 3,762,846 | 10/1973 | Chivers | 425/7 |
| 3,766,165 | 10/1973 | Rennhard | 260/209 R |
| 3,856,443 | 12/1974 | Salvi | 425/9 |
| 3,875,300 | 4/1975 | Homm et al. | 424/78 |
| 3,876,794 | 4/1975 | Rennhard | 426/152 |
| 3,925,525 | 12/1975 | LaNieve | 264/40 |
| 3,930,043 | 12/1975 | Warning et al. | 426/515 |
| 3,951,821 | 4/1976 | Davidson | 252/1 |
| 3,967,623 | 7/1976 | Butterworth et al. | 128/287 |
| 3,972,725 | 8/1976 | Nicol | 127/58 |
| 3,981,739 | 9/1976 | Dmitrovsky et al. | 127/60 |
| 3,992,265 | 11/1976 | Hansen | 195/127 |
| 4,056,364 | 11/1977 | Dmitrovsky et al. | 23/273 R |
| 4,086,418 | 4/1978 | Turbak et al. | 536/30 |
| 4,090,920 | 5/1978 | Studer, Jr. | 195/127 |
| 4,136,145 | 1/1979 | Fuchs et al. | 264/164 |
| 4,153,512 | 5/1979 | Messner et al. | 195/103.5 K |
| 4,159,210 | 6/1979 | Chen et al. | 127/29 |
| 4,293,570 | 10/1981 | Vadasz | 426/3 |
| 4,303,684 | 12/1981 | Pitchon et al. | 426/312 |
| 4,338,350 | 7/1982 | Chen et al. | 426/658 |
| 4,348,420 | 9/1982 | Lynch et al. | 426/272 |
| 4,362,757 | 12/1982 | Chen et al. | 426/599 |
| 4,371,516 | 2/1983 | Gregory et al. | 424/22 |
| 4,376,743 | 3/1983 | Dees | 264/103 |
| 4,492,685 | 1/1985 | Keith et al. | 424/28 |
| 4,496,592 | 1/1985 | Kuwahara et al. | 426/5 |
| 4,500,546 | 2/1985 | Turbak et al. | 514/781 |
| 4,511,584 | 4/1985 | Percel et al. | 426/99 |
| 4,526,525 | 7/1985 | Oiso et al. | 425/9 |
| 4,585,797 | 4/1986 | Cioca | 514/773 |
| 4,619,833 | 10/1986 | Anderson | 426/548 |
| 4,772,477 | 9/1988 | Weiss et al. | 426/99 |
| 4,793,782 | 12/1988 | Sullivan | 425/7 |
| 4,855,326 | 8/1989 | Fuisz | 514/777 |
| 4,873,085 | 10/1989 | Fuisz | 424/400 |
| 4,879,108 | 11/1989 | Yang et al. | 424/440 |
| 4,885,281 | 12/1989 | Hanstein et al. | 514/53 |
| 4,978,537 | 12/1990 | Song | 426/5 |
| 4,997,856 | 3/1991 | Fuisz | 514/777 |
| 5,011,532 | 4/1991 | Fuisz | 106/215 |
| 5,028,632 | 7/1991 | Fuisz | 514/772 |
| 5,034,421 | 7/1991 | Fuisz | 514/772 |
| 5,073,387 | 12/1991 | Whistler | 426/7 |
| 5,082,682 | 1/1992 | Peterson | 426/564 |
| 5,082,684 | 1/1992 | Fung | 426/602 |
| 5,084,295 | 1/1992 | Whelan et al. | 426/565 |
| 5,089,606 | 2/1992 | Cole et al. | 536/54 |
| 5,094,872 | 3/1992 | Furcsik et al. | 426/578 |
| 5,096,492 | 3/1992 | Fuisz | 106/215 |
| 5,236,734 | 8/1993 | Fuisz | 426/641 |
| 5,266,335 | 11/1993 | Churukuri et al. | 426/3 |
| 5,348,758 | 9/1994 | Fuisz et al. | 426/660 |
| 5,380,473 | 1/1995 | Bogue et al. | 264/11 |

FOREIGN PATENT DOCUMENTS

| | | | |
|---|---|---|---|
| 0387950A1 | 8/1990 | European Pat. Off. | B01D 1/18 |
| 88/2771 | 4/1988 | South Africa . | |
| 90/2139 | 3/1990 | South Africa . | |
| 489211 | 7/1968 | Switzerland | A23G 1/00 |
| 519858 | 5/1971 | Switzerland | A23G 1/00 |
| 2155934B | 3/1985 | United Kingdom | C13K 1/10 |
| WO91/18613 | 5/1991 | WIPO | A61K 31/74 |

SPHEROIDAL CRYSTAL SUGAR AND METHOD OF MAKING

BACKGROUND OF THE INVENTION

The present invention relates to crystalline sugar products, and, in particular, to a new form of crystalline sugar.

Crystallization is one of the oldest industrial chemical transformation processes known. Vast quantities of crystalline substances are produced for commercial purposes, e.g., in excess of $100 \times 10^6$ metric tons per year. One of the most common products prepared by crystallization is sugar.

Crystallization of sugar is complex. The growth of crystals involves simultaneous transfer of heat and mass in a multi-phase, multi-component system. While the co-existence of these conditions alone present complex control problems, fluid and particle mechanics and thermodynamic instability create further complications.

Conventional wisdom in the science of sugars teaches crystallization by supersaturation. Supersaturation requires removal of water. Cooling, evaporating, and precipitating are used. Manufacturing procedures for crystallizing sugar are heat and energy intensive. Moreover, nucleation of sugar crystals during supersaturation is relatively uncontrollable. Consequently, the size and shape of the resulting crystals are unpredictable.

The drawbacks of known sugar manufacturing procedures are especially manifested when preparing sugar having reduced-size crystals. Reduced-size crystalline sugar product is referred to herein as microcrystals. Individual particles of microcrystalline product are no greater than 50 μm.

Classification of crystallizers known in the industry follows the methods by which supersaturation is achieved. The technical aspects of procedures used for sugar crystallization are well documented, and they are generally high-energy procedures.

For example, one method of manufacturing reduced-size crystals involves grinding and sieving crystalline sugar. Grinding is energy intensive. Moreover, fracturing sugar results in a wide distribution of ground sugar crystals. The large crystals must be reground and sieved. Much of the product is lost as fines. Thus, grinding and sieving is expensive and inefficient.

U.S. Pat. No. 3,981,739 to Dmitrovsky, et al. discloses preparation of crystalline sugar from solution by 1) concentrating a solute in the presence of seed crystals added thereto, followed by 2) further removal of solvent through heating and evaporation of the stream resulting from the first stage concentration. This energy intensive procedure produces sugar crystals having an average size in the range of 325–425 microns. The Dmitrovsky, et al. '739 disclosure is a solution process which relies on nucleation by addition of seed crystals while concentrating by high heat and vacuum evaporation. The same procedure is disclosed in U.S. Pat. No. 4,056,364 to Dmitrovsky, et al.

U.S. Pat. No. 4,159,210 to Chen, et al. describes a method for preparing crystallized maple sugar product by 1) concentrating maple syrup to a solids content of about 93–98% in the presence of heat and partial vacuum, and 2) impact heating until transformation and crystallization of the syrup occur. The product may then be cooled, milled and screened to a suitable size range. The Chen, et al. '210 procedure is energy intensive, relies on "beating" to induce nucleation of the crystals, and calls for subsequent milling to obtain reduced-size crystals.

In U.S. Pat. No. 4,362,757 to Chen, et al. a crystallized sugar product and a method of preparing same are described. The method disclosed in the Chen, et al. '757 reference includes concentrating sugar syrups to a solids content of about 95% to about 98% by heating to a temperature of about 255° F. to about 300° F. The resulting concentrated syrup is maintained at a temperature not less than about 240° F. in order to prevent premature crystallization. A premix consisting of an active ingredient (e.g., a volatile flavor, an enzyme, an acidic substance such as ascorbic acid, a fruit juice concentrate, or a high invert sugar substance) is mixed with the concentrated sugar syrup. The combination is subjected to impact heating until a crystallized sugar product made up of fondant-size sucrose crystals and the active ingredient is formed which has a moisture content of less than 2.5% by weight. The Chen, et al. '757 process requires heat intensive concentrating and heating for nucleation.

A similar procedure is disclosed in U.S. Pat. No. 4,338,350 to Chen, et al. wherein a process for preparing a crystallized sugar product containing a food ingredient is described. The Chen, et al. '350 disclosure calls for concentrating a sugar syrup at a temperature range of about 250° F. to about 300° F. to a solids content of about 90 to 98% by weight. A food ingredient, such as gelatin, cocoa powder, pectin concentrate, etc., is admixed with the sugar syrup. The mixture is subjected to impact beating until a crystallized sugar product made up of aggregates of fondant-size sucrose crystals and food ingredients is formed. The Chen, et al. '350 process requires heat intensive concentrating and beating to induce crystallization.

U.S. Pat. No. 3,365,331 to Miller, U.S. Pat. No. 4,338,350 and U.S. Pat. No. 4,362,757 describe a process for crystallizing sugar, which involves impact beating a sugar solution to provide nucleation. The process involves input of considerable amount of energy and has problems directly related to temperature control.

Other disclosures include British Patent Specification No. 1 460 614 and U.S. Pat. No. 3,972,725 (Tate & Lyle Limited) which disclose a continuous process wherein a syrup solution is catastrophically nucleated and discharged into a crystallization zone. Catastrophic nucleation is achieved by subjecting the solution to shear force which can be applied in apparatus such as a colloid mill or homogenizer. The solution is discharged onto a moving band where the water must be boiled off by maintaining the material at a relatively high temperature. A related process has been disclosed in British Patent Specification 2 070 015 B and U.S. Pat. No. 4,342,603, which is used for crystallization of glucose. In the disclosed procedure, a supersaturated solution is subjected to shear force and allowed to crystallize on a belt. Both the sucrose process and the glucose process require solution processing at high temperatures and are, consequently, energy intensive.

U.S. Pat. No. 3,197,338 to Hurst, et al. discloses a process for crystallizing glucose which includes kneading a glucose solution to induce nucleation followed by crystallization to form a solid glass which is then ground. Another glucose crystallization process has been disclosed in GB 2 077 270 B in which starch hydrolyzate is concentrated by evaporation and then simultaneously crushed and mixed during crystallization while cooling. The product is further milled. These processes also require nucleating by beating a solution which includes glucose.

UK Patent Specification G B 2 155 934 B of Shukla, et al. discloses a method for crystallizing sucrose or glucose from a solution. Shukla, et al. subject a sugar solution to evaporation to produce a supersaturated sugar solution. The supersaturated solution is then subjected to shear in a continuous screw extruder to induce nucleation. The retention time of the syrup is below 25 seconds (on the average) at a temperature of 115° C. to 145° C. (239° F.–293° F.) for sucrose and 100° C.–135° C. (215° F.–275° F.) for glucose. After the syrup is subjected to progressive nucleation, Shukla, et al. pass the syrup onto a moving band to permit crystallization to continue at a gradual rate at relatively high temperature. The Shukla, et al. process requires maintenance of the solution at temperatures which do not drop below the boiling point of water.

Additional technology has been developed which relates to processing food and food ingredients. For example, a series of U.S. patents issued to Thomas E. Chivers (U.S. Pat. No. 3,762,846, U.S. Pat. No. 3,723,134, and U.S. Pat. No. 3,557,717) disclose a solution process for making candy floss from a cooked slurry or syrup. The ingredients are blended and heated at a first temperature, e.g., 200°–205° F. (93°–96° C.), to form a slurry. After forming the slurry, the batch is cooked or boiled at a substantially higher temperature, e.g., about 340° F. (171.1° C.), and thereafter discharged through an atomizing nozzle. Most of the moisture contained in the molten candy flashes off as it is discharged. The Chivers disclosures rely on dissolution of the ingredients, e.g., sugar and other ingredients, in water and then heating extensively to drive the water from the solution. Most of the water is driven off after discharging the solution. Thus, the Chivers technology suffers from drawbacks associated with sustained high temperature processing and dissolution of ingredients during processing.

Another method for processing material is disclosed in European Patent Application 0 387 950 A1 of Stork. The Stork process is a method of preparing a foam spray-dried product by collision of a stream of gas which contains dry particulate material, with a jet of droplets of a liquid solution. A liquid solution which contains at least one of the ingredients of the end product is combined with gas and heated before spraying as a jet of droplets for collision with the dry particulate. The Stork system is designed to process a low density product; it requires an elaborate equipment arrangement, and is energy intensive.

In U.S. Pat. No. 3,615,671 to Shoaf discloses a method of producing food products by encasing dry particulate food particles within a casing of spun sugar filaments. In order to enhance 1) shaping of the fibers and particles and 2) the tendency of the fibers to stick to each other with a minimum of compression, Shoaf uses a humectant in the sugar mix to be spun and controls the relative humidity of the gases surrounding the filaments as they are spun. The humectants described as useful are as follows: invert syrup or corn syrups and polyhydric alcohols, e.g., sorbitol, glycerol and pentahydric alcohols, e.g., xylitol. Shoaf is concerned with preventing crystallization of the spun sugar in order to enable the manufacturer to encase dry food particles by wrapping and compressing filaments of the spun sugar around the particles.

More recently, a trade brochure provided by Domino Sugar Corporation, Industrial Products, entitled "Co-Crystallization" (undated) describes a product in which microsized crystals form aggregates having a second ingredient disposed over the surface of each aggregate. The process for producing this new product requires that all starting materials must be in a liquid state. Therefore, solvent must be driven off by heat and/or vacuum in order to concentrate the syrup for crystalline growth. As in other solution process energy is required to transform the sugar to microsized crystals.

Inherent in the procedures set forth above, as well as other procedures known in the art, is the technical philosophy of dehydration to promote crystallization. Supersaturation, pan drying, and nucleation by agitation or chemical reaction depend on the principle of eliminating water to form crystals. A common difficulty with crystallization based on this technical underpinning has been lack of control over crystalline growth.

Thus, it would be significant advance in the art of crystallization, to provide a mechanism for crystal formation which departs from traditional dehydration, and which provide a low energy means for producing a crystalline sugar product.

Accordingly, it is an object of the present invention to enable the artisan to make a sugar product which has a predictable and uniform crystal size without energy-intensive procedures. Other objects and surprising new sugar-crystal technology are disclosed in the remainder of the Specification.

SUMMARY OF THE INVENTION

The present invention is a new form of crystalline sugar as well as a method of making same. The new crystalline sugar consists of substantially spheroidal polycrystallite structures. The polycrystallite structures, in turn, are made of sugar crystallites which are quite small, i.e., on the order of less than 10 µm, and are quite uniform in size. In fact, the spheroidal polycrystallite structures can be monodispersed, and the crystallites themselves are monodispersed as defined hereinbelow. In a preferred embodiment of the present invention, the spheroidal polycrystallite structures are microcrystalline, i.e., have a greatest dimension of not more than about 50 µm.

Contrary to the teachings in the art of sugar crystallization, the new sugar product is prepared in accordance with the present invention by adding water to amorphous sugar. Amorphous sugar as used herein means a sugar stock which contain a high percentage of amorphism, i.e., greater than 50% by weight, and preferably greater than 70% by weight of the sugar stock is amorphous. The unique procedure of this invention includes contacting amorphous sugar with a non-aqueous sugar-nondissoluble liquid and water so that the water is made available to the amorphous sugar at a controlled rate and in an amount which permits growth of the spheroidal polycrystallite structures.

While the present invention primarily concerns sugars as defined herein, it is also intended to include processing (and products therefrom) any amorphous solid form of a solvent-soluble compound which is capable of forming crystals. Such compounds may include lactose, polydextrose, maltodextrins, etc. Preferably the solvent for the process and product(s) herein is water.

Amorphous sugar can be provided by shearform processing a sugar-containing feedstock. A shearform process according to the present invention is one in which a feedstock is subjected to shear and heat simultaneously in order to obtain flash flow. One shearform process includes subjecting a feedstock containing sugar to shear created by high speed spinning on a spinning head. The spinning head casts the material outwardly as the feedstock undergoes flash flow. Flash flow is created as a consequence of the simultaneous application of heat and shear. An alternative shearform process includes heating a non-solubilized feedstock having a sugar carrier sufficiently to provide internal flow. The feedstock is ejected while the sugar possesses internal flow, and is then subjected to disruptive fluid shear force to form multiple masses of carrier. Other methods are contemplated which provide the same critical conditions of heat and shear so that a substantially solid feedstock which contains sugar can be transformed physically and/or chemically from a solid structure to an essentially amorphous solid structure.

An additive can be included in the amorphous sugar and become part of the resulting polycrystallite structures and the crystallites themselves. This is referred to herein as co-crystallization. When such an additive is provided, it is included without reducing the amorphism of the sugar and without deteriorating the resulting polycrystallite structures. Additives contemplated for use herein, include, but are not limited to, flavorants, bio-affecting agents, dyes, fragrances, food products, food ingredients, and other compatible agents. Flavorants in the present invention includes sweeteners of all types, natural and synthetic.

In a further embodiment of the present invention, co-crystallization can be effected by using an additive, especially a bio-affecting agent, as a nucleating agent. This is another mode of co-crystallizing because the nonsugar additive is introduced during crystallization—not during formation of amorphous sugar. The bio-affecting agent is made available in the solvent (e.g., water) which is used to initiate and promulgate growth of sugar crystals from amorphous sugar. Consequently, the bio-affecting agent actually serves as a nucleating agent.

A non-aqueous sugar-nondissoluble liquid means a liquid which contains substantially no water and in which sugar does not dissolve, i.e., less than 1 gr. of sugar will dissolve in 50 ml of the liquid. One such liquid is ethanol. The non-aqueous sugar-nondissoluble liquid can also be a blend of two or more nonsolvents.

In a preferred embodiment of the present invention, the non-aqueous sugar non-dissoluble liquid and water form an azeotrope, and, in the most preferred embodiment of the present invention, the water and the liquid are combined within an azeotropic range. An azeotropic mixture is a mixture wherein distillates of the mixture have the same composition of components as does the liquid mixture. Thus, in the case of water and another liquid medium, the mixture will distil at the same ratio of components which are present in the mixture.

The present invention involves the use of ambient systems which include a nondissoluble liquid and a solvent component. In all cases herein the components possess their salient characteristics, i.e., nondissolubility and solvent characteristics, at room temperature, e.g., 28°–32° C.

Water is provided in the non-aqueous sugar-nondissoluble liquid in an amount sufficient to enable the amorphous sugar to be controllably crystallized to form spheroidal polycrystallite structures. It has been found in the preferred mode that water is present in an amount not greater that about 5%, and preferably not greater than about 2%.

Other effects can be achieved by including a surfactant in the feedstock which is used to make the amorphous sugar. By using a surfactant, a uniform tiny crystal product can be made with a high degree of predictability. Lecithin has been found to be the preferred surfactant at this time. It is expected that other surface active agents will be identified which enhances the procedure and product of the present invention, and it is intended to include such additional surface active agents within the scope of the claimed invention.

In order to obtain as a separate product the crystallites which combine to form the polycrystallite structure, the spheroidal polycrystallites are disintegrated. This has been achieved by contacting the spheroidal polycrystallite structures with a sugar-saturated liquid, e.g., greater than about 67% sugar (sucrose). The resulting crystallites are highly uniform, i.e., monodispersed, and have a very tiny size, i.e., on the order of about 5 μm.

A further manifestation of the present invention is a comestible composition which can be used as a coating or filler for baked goods. Coatings and fillers as used herein means a non-baked portion of an edible product, such as cookie fillings, cake fillings (e.g., Twinkie™ fillings, etc.) icings, and other coatings. These coatings and fillings include either the spheroidal polycrystallites or crystallites or both, and other ingredients which preserve organoleptic properties, e.g., texture, moisture level, prevention of crystallization, et al. Additional ingredients employed to achieve the preservation of the coatings and fillers include, but are not limited to, gums, humectants, fats, and flavors (including sweeteners). The present invention includes these compositions.

As a result of the present invention an entirely new crystalline form has been provided. This crystalline form has been found to be extremely useful in products which require a uniform crystal sugar product. For example, a new fondant consisting of substantially spheroidal polycrystallite structures can be prepared. In yet a further preferred embodiment, a fondant product can be prepared which uses monodispersed sugar crystallites. The resulting product is amazingly smooth and flowable, and has an entirely different microscopic composition from any known fondant product.

One of the distinct advantages of the present invention is that the size range of the product can be selected for the intended use. Moreover, the nature of the process of the present invention enables the artisan to make a crystalline product of a particular size and shape with a very high degree of predictability. Reduced-size crystals can be efficiently produced without the use of energy-intensive grinding and sieving. This is a significant departure from crystalline products and processes of the past.

As a result of the present invention a new fat mimetic ingredient is provided for use in foods, e.g., fondants, frosting, fillers for baked goods—especially cookie fillers, etc.

Moreover, an extremely efficient tableting vehicle is provided. Active agent can be incorporated into the crystalline product, and the crystalline product, (with or without active agent), can be used as an excipient.

The present invention has uniquely harnessed the natural drive of matter to seek and maintain a lower energy state, to create a process for controlled crystalline growth as well as new product resulting therefrom. Material which has a natural crystalline structure in its lowest entropy state is transformed to an increased entropy state when it is made amorphous. In the amorphous condition the material possesses a natural tendency to attain a lower energy state—i.e., the crystalline form of the material. The inventors herein have harnessed this natural tendency of matter to drive controlled crystallization. This has been achieved by providing an essentially non-solvent system in which a controlled amount of solvent (for the particular matter) is made available to permit controlled crystallization. The variety of procedures and products resulting from harnessing of nature's tendency to seek its lowest entropy state are boundless, and the present claims cover any procedure which utilizes the principles set forth herein.

For a better understanding of the present invention, reference is made to the Drawings, the following Detailed Description and non-limiting examples. The scope of the invention is described in the claims which follow the detailed description.

DETAILED DESCRIPTION OF THE INVENTION

Figure 1:
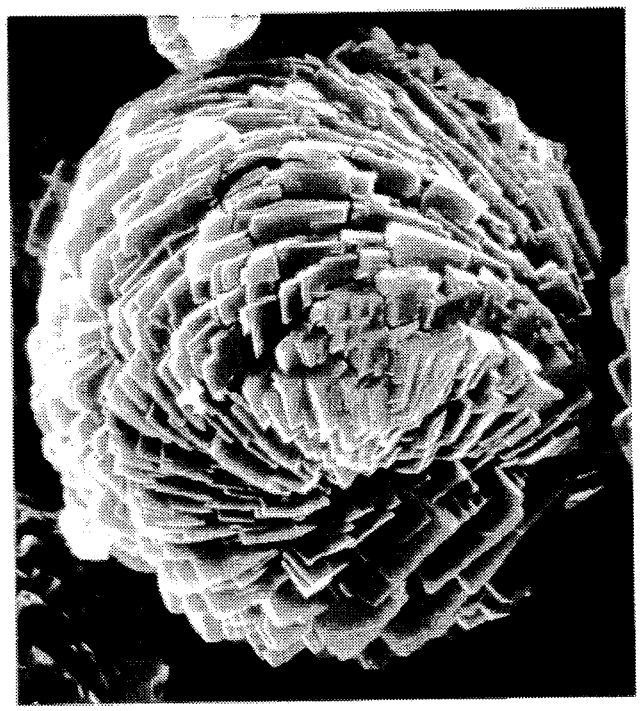
FIG. 1 is a detailed photomicrograph of the unique spheroidal polycrystallite of the present invention.

The present invention is a new crystalline sugar in the form of a substantially spheroidal polycrystallite structure. See FIG. 1 which is a photomicrograph of spheroidal polycrystallites produced in accordance with the present invention shown at 3.0K magnification. By substantially spheroidal is meant that the structure is formed with a spherical center. However, the final crystalline product can also assume the shape of a dome or a raspberry-like structure. Many of the structures will be completely spheroidal. In any event, substantially spheroidal is intended to include all such polycrystallite structures which possess a spheroidal center.

The term polycrystallite, is meant to describe the spheroids as being composed of many tiny crystallites. The spheroidal polycrystallites of the present invention have at least 20, but preferably more, crystallites arranged around a spheroidal center. In fact, upon microscopic inspection of the structures, one can detect the individual tiny crystallites arranged as a "coat of mail" about a spherical center. See FIG. 1. These crystallites are on the order of several angstroms, i.e., less than 10 μm, and preferably less than 5 μm. The polycrystallite spheroids can be disintegrated to release the crystallites. For example, crystallites can be released by contact with a saturated sugar solution. In a preferred embodiment, the spheroidal polycrystallites of the present invention can be determined by identifying at least 20 crystallites while dissolving the spheroids with a saturated sugar solution. This crystallite product has been found to be ideal for formation of a fondant, e.g., cake icing, confectionery fillings, coated candy fondants (such as chocolate coated), etc. The properties of the polycrystallite sugar product make it ideal to replace all (or some portion) of the fat in comestibles such as frostings, fillings, etc. The organoleptic sensations created by fat are closely emulated or replaced by use of the present product.

The spheroidal polycrystallites of the present invention have a truly unique capability of building the viscosity of a fondant composition at a relatively low sugar concentration. A fondant is a soft, creamy candy made of sugar, and is normally used as a filling for other candies. For example, if it is normally necessary to include 67% by weight of commercially-available fondant sugar to achieve the correct viscosity in a fondant, only about 37% by weight (or about ½ the amount of the commercial fondant sugar) of the polycrystallite sugar is required to achieve the same. This is a truly remarkable effect which is further described in the examples.

Another unique feature of a preferred embodiment of the present invention is that the spheroidal polycrystallite structures can be monodispersed. Monodispersion of spheroidal polycrystallites means non-agglomerated polycrystallites. Even the crystallites themselves are monodispersed. Monodispersed as used herein refers to the production of a highly uniform crystalline product. As previously explained, crystalline sugar prepared by methods known in the art result in a wide variety of crystal sizes. This is due to many factors, all of which contribute to the basic lack of control over the nucleation and growth of crystals. In the present invention, however, the new spheroidal polycrystallite structures are grown to a predictably uniform size.

"Monodispersed" as used herein means that at least about 60% by weight, preferably at least 80% and most preferably at least 90%, of the crystals have a largest diameter which is within 60% of the mean crystal diameter. Crystal diameter is that dimension which is the greatest straight line dimension in the largest plane taken through a three dimensional crystal.

Figure 2:
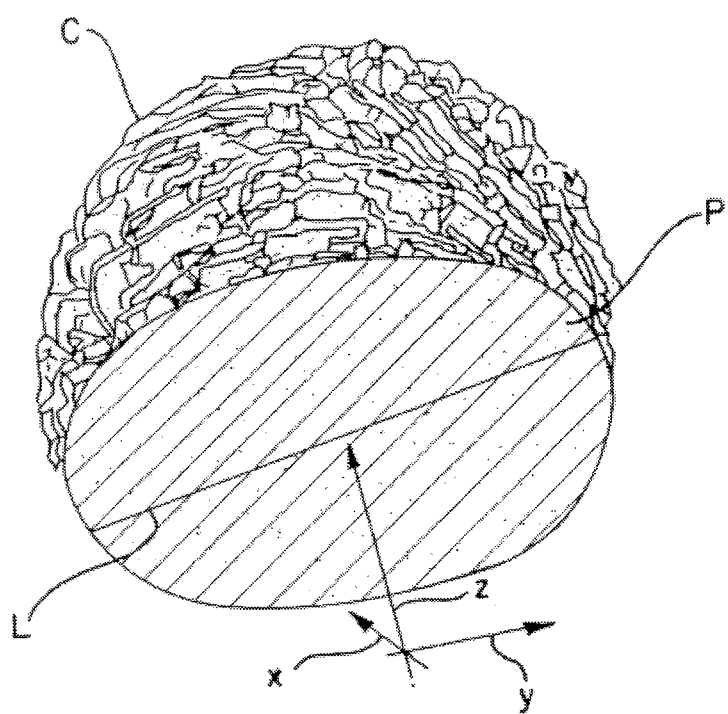
FIG. 2 is a schematic representation of the polycrystallite structure of the present invention in partial cross-section.

Referring to FIG. 2, if one considers a crystal C which has three dimensions in the x, y, and z directions, the crystal diameter is the greatest straight line dimension L in the largest plane P through the crystal.

In yet a further preferred embodiment mono-dispersibility means that at least 60% of the crystals are within 50% of the mean crystal diameter, and in a most preferred embodiment within 40% of the mean crystal diameter.

In view of the fact that such a significant percentage of the crystals can be grown to within a very uniform size range, significant advantages are obtained in the use of the product.

The process of the present invention is quite unique in that it employs a procedure which is directly opposite the classic teaching of the sugar technology to form a crystal by concentration and/or supersaturating sugar from a solution. In fact, the present invention employs a procedure which requires controlled addition of a sugar solvent, preferably water. Water is controllably added to form the unique crystals and promote unique crystalline growth claimed herein.

In the preferred embodiment of the present invention, the amorphous sugar is provided by shearform processing a sugar-containing feedstock. In the present invention, amorphous sugar is formed from "sugars." "Sugars" are those substances which are based on simple crystalline mono- and di-saccharide structures, i.e., based on $C_5$ and $C_6$ sugar structures. "Sugars" include sucrose, fructose, lactose, maltose, and sugar alcohols such as sorbitol, mannitol, maltitol, etc. The sugar of choice in the present invention is sucrose.

A shearform sugar product is a substantially amorphous sugar which results from subjecting sugar to heat and shear sufficient to transform crystalline sugar to amorphous sugar without the use of a solution. Thus, in the sense of the present invention, a shearform sugar product is characterized as a sugar product resulting from a non-solubilized sugar. It can be the starting material for forming the unique crystalline product of the present invention. However, any amorphous sugar can be used.

This entire concept is directly contrary to the prior art which specifically teaches the artisan to crystallize sugar by eliminating or dehydrating solvent by driving it off with heat and/or vacuum.

A further aspect of the present invention is co-crystallization. Any compatible additive can be included internally in the crystallite or polycrystallite structures of the present invention so that the end product includes the additive(s). Such additives can be selected from the group consisting of flavorants, bio-affecting agents, dyes, fragrances, food products, food ingredients, and other agents which are compatible. Compatible means the additives can be included in the amorphous sugar without destruction of the amorphism, and can be included in the crystallite and polycrystallite structures without deterioration thereof.

A non-limiting list of bio-affecting agents is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, physchotropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-phsychotics, anti-tumor drugs, anticoagulants, antithrombotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

The present invention is particularly useful in providing a new delivery system for inhalants. Inhalants must be formed of minute particles which are rapidly absorbed by the patient. Thus, since sugar is quickly dissolved at body temperature, inhalants co-crystallized with the unique tiny highly-uniform product of the present invention can be easily delivered as a tiny particulate which is rapidly absorbed by the body.

Any amorphous sugar can be used, but the present preferred embodiments include the use of amorphous shearform product. The shearform product of the present invention can be made on machines such as those used for making cotton candy. In these machines, sugar is introduced to a spinner head in which it is subjected to heat and shear created by centrifugal force from the spinning head. Disclosures which relate to spinning substances include U.S. Pat. Nos. 4,855,326, 4,873,085, 5,034,421, 4,997,856, and 5,028,632.

Examples in the U.S Patents listed above describe processing feedstock material by subjecting it to high speed spinning on a spinning head in which the substance is also subjected to heating by a heating element. The change of temperatures is quite large, which is believed to be occasioned by the spinning head quickly and efficiently spreading the feedstock material against the heating element circumferentially disposed around the perimeter of the spinning head. Thus, extensive surface contact of the feedstock against the heating element is provided. An additive can be included in the feedstock so that co-crystallization results when processed according to the present invention.

More recently, commonly owned co-pending application entitled "Process for Making Shearform Matrix," filed on Oct. 23, 1992 and assigned U.S. application Ser. No. 965,804, discloses another process for making shearform matrix by subjecting non-solubilized feedstock to heat sufficient to induce internal flow, ejecting a stream of the feedstock while possessing internal flow, and then subjecting it to disruptive fluid shear force which separates it into separate parts or masses having a transformed morphology. The product is amorphous. Other ingredients can be included in the material so that when it is used in the present invention, co-crystallization will occur.

The amorphous sugar, with or without the additive, is then contacted with a non-aqueous sugar-nondissoluble liquid, and water. The purpose of contacting amorphous sugar with water in the environment of the non-aqueous sugar-nondissoluble liquid is to achieve highly controlled contact of the amorphous sugar with moisture. In this way the unique spheroidal polycrystallite structures can be formed. In a preferred embodiment, the non-aqueous sugar-nondissoluble liquid is one which combines with water to form an azeotrope. An azeotrope is a liquid mixture which produces distillates having the same composition as the liquid mixture. A preferred non-aqueous sugar-nondissoluble liquid used in the present invention is ethanol. Ethanol forms an azeotropic mixture with water. It is believed that the affinity of ethanol to form a relatively inseparable combination with water enhances the control exerted over the contact of water with the amorphous sugar. In any event, the water is presented to the amorphous sugar at a rate and in an amount which permits the spheroidal polycrystallite growth.

Generally, water is made available in ethanol by providing a 5% water in ethanol mixture and preferably less than 1% water, at a temperature of about −10° C. to about 40° C.

As yet a further modification to the present invention, a surfactant can be included in the feedstock which forms the amorphous sugar. The use of a surface active agent in the feedstock enables the practitioner to exercise even greater control over crystal formation. It has been found that greater uniformity of crystal size is achieved. Furthermore, formation of aggregates is prevented by use of a surfactant. Finally, greater control of the size of the crystalline spheroids is also achieved. The preferred surfactant is presently lecithin. Lecithin can be included in the feedstock in an amount of from about 0.1% to about 5.0% by weight.

A further aspect of the present invention is a composition which include either the spheroidal polycrystallites or the crystallites or a combination of both, and which are used as fillings and/or coatings for baked goods. These ingredients, which generally preserve the organoleptic properties of the compositions, can include gums, humectants, fats, and flavors (including sweeteners). Other ingredients may be used, and the present invention is intended to include all such compositions which incorporate spheroidal polycrystallites and/or crystallites.

Gums are generally considered carbohydrate polymers of high molecular weight, and include both natural gums and mucilages such as acacia, agar, alginic acid, carrageenan, guar gum, guaiac gum, karaya gum, tragacanth gum, xanthan gum, locust bean gum, and alginates, e.g., calcium alginate, potassium alginate, and sodium alginate. Gums also refer to cellulosic gums which include hydroxypropyl methylcellulose, hydroxyethyl cellulose, methyl cellulose, carboxymethyl cellulose and hydroxymethyl cellulose.

Humectants are considered those agents which retain or help to retain moisture in foods and include glycerine, potassium polymetaphosphate, propylene glycol, polyethylene glycol, sodium chloride, sorbitol, invert sugar and glycerol triacetate (triacetin), corn syrup and corn syrup solids.

Fats are another class of ingredients which can be used in the compositions of the present invention and generally include mono-, di-, and tri- glyceryl esters of higher chain fatty acids, e.g., stearic and palmitic, or mixtures thereof, and can be solid or liquid. Fats can be derived from plants or animals.

With respect to flavors, the compositions of the present invention include but are not limited to, flavors such as spices, acid flavors, sweeteners both synthetic and natural. Spice oleoresins are included in the compositions of the present inventions.

EXAMPLES

In the following examples, amorphous sugar has been provided by spinning sucrose in a spinning machine operated at about 160° C. and spun at a rate of about 3600 rpm. The product was in the form of a sugar floss.

ETHANOL EXAMPLES

Granulated sucrose was processed in a spinning device as set forth herein above to produce an amorphous fibrous cotton structure (floss). The volume of the floss was reduced by subjecting it to processing in a high speed mixer to break the fibers into smaller pieces.

Non-aqueous sugar-nondissoluble liquid was provided in the form of anhydrous ethanol, i.e., 200 proof ethanol. Water was carefully introduced to the ethanol to create 11 different compositions ranging in water content from 0.08 to 4.8% on weight basis. The compositions have been set forth below in an Ethanol/Water Table.

| WATER/ETHANOL TABLE Water % in Ethanol vs. Particle Size Particle Size (Microns) | | |
|---|---|---|
| Water % | 10%[1] | 50%[1] |
| .08 | 7.73 | 22.98 |
| 0.62 | 9.34 | 24.26 |
| 1.02 | 8.51 | 22.43 |
| 1.53 | 11.35 | 30.43 |
| 1.97 | 12.58 | 29.60 |
| 2.44 | 18.84 | 42.70 |
| 2.90 | 19.05 | 37.96 |
| 3.17 | 16.54 | 34.19 |
| 3.72 | 20.94 | 43.10 |
| 4.14 | 20.89 | 40.26 |
| 4.80 | 20.56 | 43.64 |

[1]Average of three measurements

A 2.5 gram sample of floss was added to 35 grams of each of the anhydrous ethanol/water compositions. Each mixture was stirred for about 1 minute and then vacuum filtered to remove the ethanol and recover crystal samples. The total contact time was about two (2) minutes.

Photomicrographs of the crystals were made which show the unique spheroidal polycrystallite structure. The crystals resulting from the procedure set forth above are depicted in FIG. 1.

Figure 3:
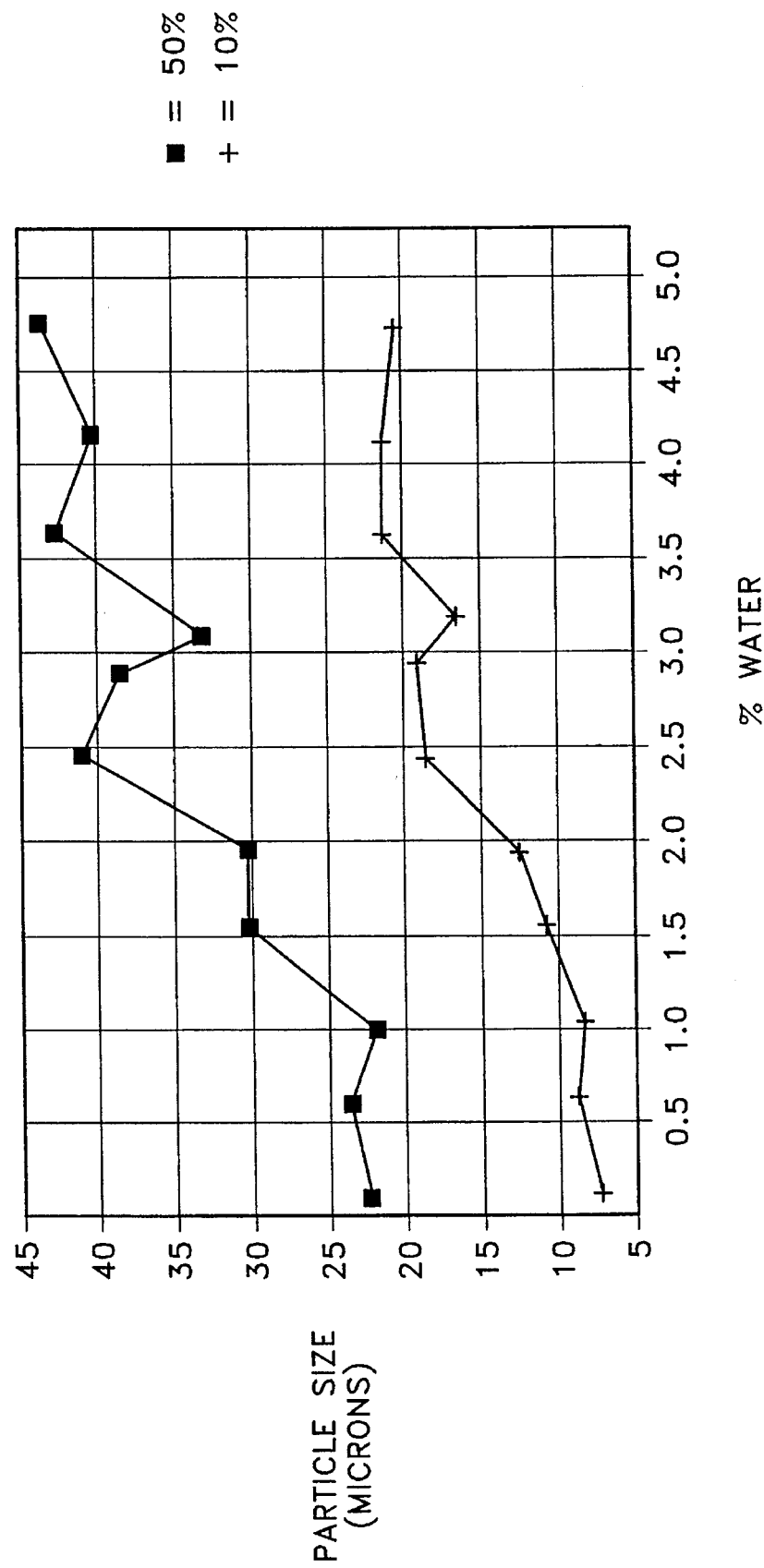
FIG. 3 is a graphical representation of the results of experiments conducted to determine the effect of percentage of water content in non-aqueous sugar-nondissoluble liquid.

Each of the crystal samples were analyzed in a Microtrac FRA particle size analyzer. The analysis was conducted by three scans of 15 seconds each and average values were recorded. The results are reported in the Water/Ethanol Table and depicted in FIG. 3. The predominant particle size was measured as a percentage of particles below a certain size. These sizes are entered in the table and on the graph in FIG. 3 as a function of the ethanol/water composition in which they were produced. The results show that crystals produced by any given ethanol/water composition had 50% of its particles below a certain particle size, while 10% of the crystals were below a smaller size.

The results are consistent. They show that an increase in percent of water corresponds to an increase in the size of the crystals which resulted therefrom. Thus, for example, 50% of the crystals grown at 0.08% water content were below a particle micron size of about 23 μm, while 10% had a particle micron size below 8 μm.

Figure 4:
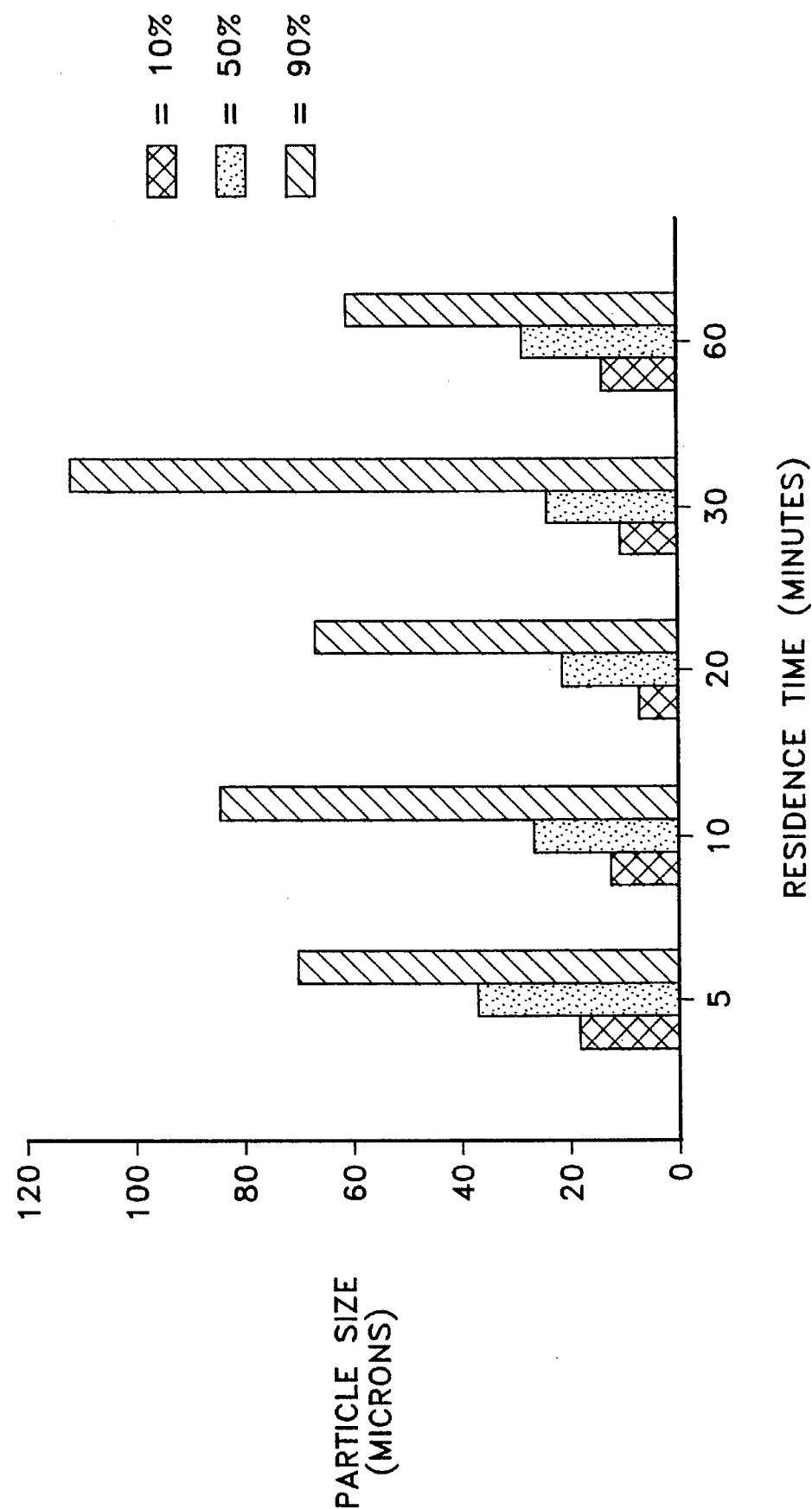
FIG. 4 is a graphical representation of the effects of residence time of amorphous sugar in non-aqueous sugar-nondissoluble liquid at less than 1.0% water content.

Further experiments were conducted in which crystal growth was measured as a function of contact time with anhydrous ethanol and less than 1.0% water. Referring now to FIG. 4, the crystal size has been depicted as it corresponds to the time of exposure to the ethanol/water composition. One can see that after 5 minutes 90% of the particles had a size of about 68 μm or less, 50% of the particles were of a particle size of about 38 μm or less, and 10% of the crystal had a size of about 18 μm or less. The graph of FIG. 4 shows that up to sixty (60) minutes of contact time resulted in little change in crystal size at the 50% range.

The results of the ethanol/water experiments show unique spheroidal polycrystallite structure. The crystals are spheroidal in size and shape (e.g., dome, raspberry-like, etc.). Moreover, the results of the above experiments show that the crystal sizes are highly uniform, i.e., monodispersed.

Furthermore, the crystals can be very quickly produced, i.e., within 30 seconds for the smaller size crystals. This is a significant departure from procedures known in the art which require high energy-consuming steps such as heat-intensive drying and application of vacuum to remove quantities of solvent, usually water, from a solution of sugar.

Moreover, the ethanol used in each of the crystallizations can be recovered and recycled for use again at the desired water content range. For example, the ethanol used in several of the experiments set forth above was recycled after filtration and analyzed after the first, fifth and tenth runs. The results of these tests show that after the first run, the ethanol contained 0.82% water; after the fifth run, the ethanol gained water to increase the overall content to only 2.613%, while after the tenth run, the water content increased to only 2.779%. The average crystal size of each of these runs was only about 25 μm.

Thus, not only does the present procedure produce a unique crystal never before realized in the sugar industry, but the procedure has reduced the energy required to drive off solvent, and the crystallization medium is recycled with a high degree of efficiency and reusability.

NON-ETHANOL EXAMPLES

Acetone/Water

Another sample was run using acetone as the non-aqueous sugar-nondissolving liquid. Water was added to a content of 0.39%. To 9.7 grams of the acetone/water above composition 0.1 gram of sucrose floss was added. After only fifteen (15) minutes the unique crystallization of the present invention occurred. There was some rod crystals resulting from the crystallization, but a significant amount of spheroidal polycrystallite was also formed.

Benzene/Water

Another sample was run using benzene having a water content of about 0.105%. The sugar floss was added to the benzene/water composition in an amount of about 5.0 grams. Again, the unique crystallization occurred but at a rate somewhat slower than the ethanol/water composition. Basically, it took about three (3) weeks to obtain maximum crystallization.

In order to provide a highly accelerated and efficient procedure, it is presently believed that an anhydrous ethanol/water combination is the most preferred. The water should be included in the ethanol in an amount of not greater than 5%, preferably less than 3%, and most preferably less than 2%. Floss should be added in an amount such that the floss to ethanol ratio is not greater than 2 to 1 or not less than 1 to 120 by weight.

SURFACTANT EXAMPLES

Further experiments were conducted in which the surfactant lecithin was used as part of the sugar feedstock which was processed to form the amorphous sugar. Specifically, 0.5% of lecithin was included in the sucrose feedstock. The material was processed using a high speed spinning apparatus at a temperature of about 160° C. and a spinning speed of about 3600 rpm. The product resulting from the flash flow procedure set forth above had the appearance of cotton candy.

The floss product resulting from the above procedure was then introduced to anhydrous ethanol which contained less than 1.0% water. A 1 gram sample of floss was immersed in 14 grams of the anhydrous ethanol/water composition at room temperature for a time period of about 2 minutes. The results indicated a highly uniform reduced-size polycrystallite spheroidal structure, which did not tend to aggregate. In fact, the polycrystallites were on the order of about 4 µm. The tendency to aggregate is inherent in the growth of sugar crystals. The use of the surfactant reduced the tendency to aggregate.

Moreover, the size range was smaller than that experienced with the procedures using an amorphous sugar without a surfactant. Furthermore, the particle size was even more uniform than was the particle size resulting from the growth of polycrystallites which did not include a surfactant.

In conclusion, therefore, it is believed that the use of surfactant (especially lecithin) even further enhances the ability of the artisan to controllably grow uniform spheroidal polycrystallites having even smaller dimensions than that experienced in the absence of the surfactant. This capability provides the artisan with yet a further tool to engineer a product which is desired for use in sugar technology.

CRYSTALLITE EXAMPLES

In order to produce crystallites from the polycrystallite structures prepared in accordance with the examples set forth above, water which had previously been essentially saturated was contacted with the spheroidal polycrystallite structures. In one case, saturated water was provided with an approximately 67% sucrose content. Water with 67% sucrose is essentially sugar saturated. As a result of contacting saturated water solution with the polycrystallite product, the polycrystallite disintegrated, dispersing the crystallites throughout the solution. The crystallites were made available for use in the solution as a monodispersed crystallite product—to impart smooth fat-like mouthfeel.

Figure 5A:
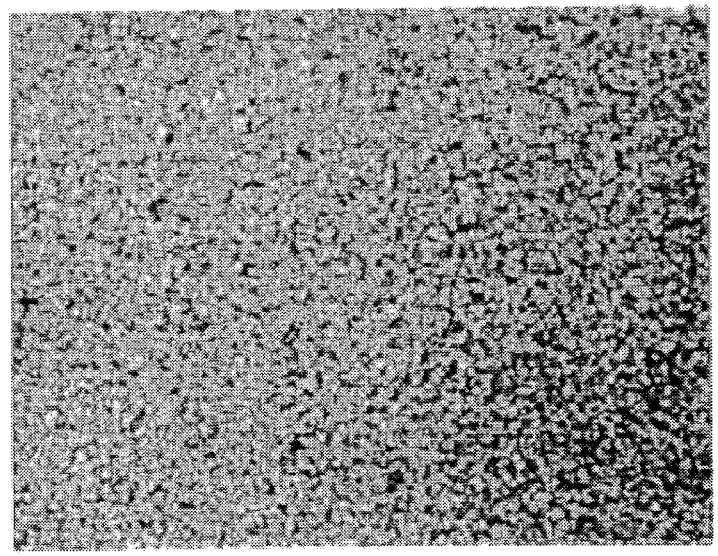
FIG. 5a and 5b are photomicrographs which compare the unique crystallites produced in accordance with the present invention to fondant crystals available from processes known in the art.
Figure 5B:
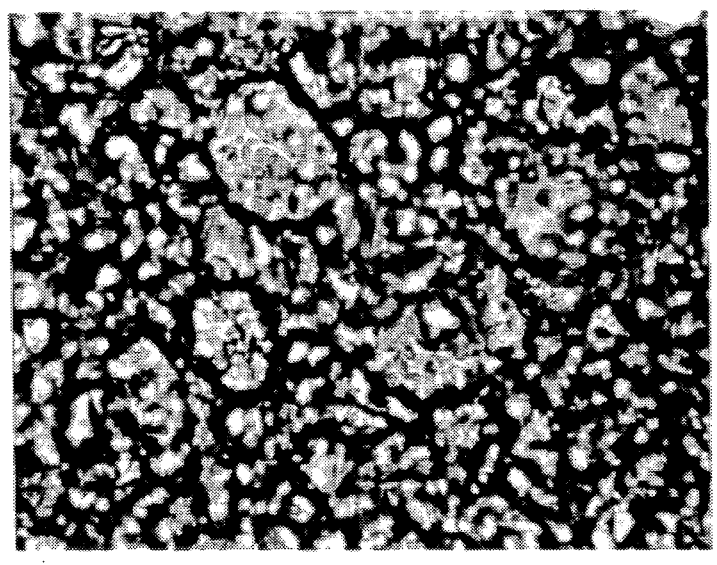

Another experiment was conducted in which a polycrystallite product was added to 8.5% water. The polycrystallite structures were disintegrated releasing the crystallites into the composition. FIG. 5a is a photomicrograph taken at 450 magnification of the crystallites in a composition which can be used as a fondant. In order to show the efficacy of this procedure and product, a photomicrograph taken at 450 magnification of a fondant product prepared with fondant sugar known in the art is shown in FIG. 5b. The comparison is dramatic. A fondant product prepared using crystallites of the present invention appears to have a sandy consistency. The fondant prepared with the fondant sugar known in the art has a gravel-like consistency. Clearly the sandy consistency is much preferred for purposes of smoothness and flowability in a fondant composition.

FONDANT EXAMPLES

Examples of fondant cremes were prepared by addition of water to the unique polycrystallite sugar prepared in accordance with the present invention and compared to fondant cremes prepared from commercial sugar supplied as Amerfond™ sugar from Amstar. Both fondant cremes were prepared by using other fondant ingredients in accordance with the table set forth below.

| | FONDANT TABLE | |
|---|---|---|
| Ingredient | Inventive Fondant (Grams) | Commercial Fondant (Grams) |
| Corn Syrup | 14.00 | 14.00 |
| Flavor, Raspberry | 0.36 | 0.36 |
| Citric Acid | 0.80 | 0.80 |
| Invertase | 0.61 | 0.61 |
| Color, Red (10%) FDC # 40 | Trace | Trace |

Water was added in order to achieve the correct viscosity for preparing fondant-containing confections, i.e., chocolate coated fondant candy.

Surprisingly, it was found that the amount of inventive sugar required to obtain the correct viscosity was about 50% of the amount of commercial sugar required to achieve the same viscosity. In particular, it was found that only about 37 grams of the inventive sugar was required to attain a viscosity of about 1.8 centipoises, whereas about 67 grams by weight of the commercial sugar was required to attain the same viscosity.

The compositions were prepared by dry mixing the ingredients and then adding water while mixing. Water was added until the consistency of the composition attained a creamy smoothness. The fondant composition was then allowed to set before rolling and permitting to become firm.

As another interesting and unusual result, it was discovered that the creme prepared with the inventive sugar required only fifteen (15) minutes of time to set to a firmness sufficient to handle, whereas the fondant creme prepared with the commercial sugar required thirty (30) minutes to set sufficiently for handling and dipping.

The cremes were then processed by dipping into chocolate. The cremes prepared with the sugar product of the present invention retained its shape better while dipping. Moreover, immediately after the cremes were produced the inventive cremes had a smoother texture which was retained over at least a five (5) day period.

The results of the fondant experiments were striking in that the amount of sugar required as well as the product itself were significantly enhanced by use of the polycrystalline sugar of the present invention.

FAT MIMETIC EXAMPLES

Examples were also prepared in order to test the efficacy of the polycrystallite sugar used in a confectionery filling which relies on fat as a medium for the organoleptic quality of the product. In particular, cookie fillings include fat in order to provide the texture, firmness, quality, and mouthfeel necessary to be used as a cookie filling.

In order to test a cookie filling prepared with the present invention, a formulation was prepared which included a total of 84.94% sucrose. In order to prepare this composition, 35 grams of the polycrystallite spheroid product was combined with 29.4 grams of a saturated sucrose solution. The saturated sucrose solution contained 30.59 grams of sucrose and 15.06 grams of water, i.e., 67% sucrose.

4.8 gram samples were used to provide a filler between two Oreo™ cookie halves. The cookies prepared in accordance with the present invention were tasted by a test panel. The results revealed that the cookies prepared with the polycrystallite spheroid product of the present invention had a much cleaner mouthfeel, and were smoother and creamier than the normal Oreo™ cookie filling. The commercial Oreo™ cookie filling contains a great deal of fat. The composition of the present invention includes no fat.

Consequently, confectionery fillings for products can be prepared using the new crystals of the present invention and in order to eliminate or replace fat in such fillings. Other and further uses will be apparent to those skilled in the art and it is intended to include all such other uses as come within the scope of the present invention.

CAKE ICING EXAMPLES

Further experiments were run to compare cake icings prepared with the spheroidal polycrystallite sugar of the present invention against commercial icings. Cake icing was prepared in accordance with the formulas set forth below in the table.

| Ingredient | CAKE ICING | |
| --- | --- | --- |
| | Inventive Icing (Grams) | Commercial Icing (Grams) |
| Commercial Fondant Sugar | — | 227.0 |
| Inventive Sugar | 227.0 | |
| Corn Syrup, 42 D.E. | 9.0 | 9.0 |
| Agar | 1.18 | 1.18 |
| Simple Syrup 66 Brix. Soln. | 220.0 | 190.0 |

The sugars were placed in separate mixing vessels and blended with agar, after which the corn syrup was added. The simple sugar solutions were then added until the desired consistency was achieved. As been noted before, the compositions prepared with the polycrystallite of the present invention required additional simple syrup because of the capacity of the polycrystallite to include more water. The yield of icing was at least 7% greater using the polycrystallite sugar of the present invention. Thus, significantly less sugar is required when using the present invention.

The product using the polycrystallite spheroid sugar of the present invention was whiter, cleaner tasting, smoother texture, and had a higher yield when compared to the commercial counterpart. It has been found that high quality fondant and fondant products can be produced without the requirement of making a fondant using conventional cooking, cooling and pulling equipment. Mere mixing in correct proportions has been found to be adequate to prepare a high quality product using the present invention.

DONUT ICING EXAMPLES

The following example was an icing prepared for dipping baked goods or other comestibles in order to provide a coating. The present examples were used to provide a frosting for donuts.

The frosting was prepared in accordance with the formula set forth in the table.

| Ingredient | COATING FORMULATION | |
| --- | --- | --- |
| | Inventive Coating (Grams) | Commercial Coating (Grams) |
| Commercial Fondant Sugar | — | 454 |
| Inventive Sugar | 454 | — |
| Corn Syrup 42 D.E. | 18 | 18 |
| Water | 76 | 60 |

The ingredients were separately added while mixing hot water and dry sugar. Afterward, corn syrup solids were added and additional water in order to provide the correct consistency.

As can be seen, the sugar of the present invention required a significant amount of additional water and resulted in a significantly larger batch as a consequence. Thus, the coating prepared in accordance with the present invention has a higher yield than does a coating composition prepared with conventional fondant sugar.

Both coatings were used as icing for donuts by dipping the donuts into the coating. The set time of the coating prepared in accordance with the present invention was much better. Specifically, the consistency of the coating permitted easier immersion of a donut, and the coating set to a firmer and more appealing consistency, and adhered better to the donut surface in a shorter period of time.

TABLET EXAMPLES

In order to show the efficacy of the present invention in various comestible forms, experiments were run to determine its usefulness in tableting. In particular, 500 milligram samples of the spheroidal polycrystalline sugar product was added to a tablet press and pressed under 1.5 tons of pressure. Tablets were formed directly from the spheroidal polycrystallite product without the need for an additional excipient or, for that matter, any other tableting aid or vehicle.

The tablets formed were glossy and hard. However, when consumed, the hard tablets dissolved quickly in the oral cavity.

It appears that the polycrystallite product prepared in accordance with the present invention can be tableted directly without the need for a tableting aid. Moreover, tableting the new product does not require wet or dry granulation, or agglomeration. Thus, the spheroidal polycrystallite product could be used directly to provide tablets or, indeed as an excipient for preparing other tablets with other materials.

The ready dissolution which occurs in the oral cavity is probably attributable to the unique small polycrystallite structure. However, it is not intended that the present invention is in anyway limited by the hypotheses set forth herein.

Thus, while there had been described what are presently believed to be the preferred embodiments of the present invention, those skilled in the art will appreciate that other and further modifications can be made without departing from the true scope of the invention, and it is intended to include all such modifications and changes as come within the scope of the claims as appended herein.

What is claimed is:

1. A method of making a sugar product comprising:
   controllably adding water to amorphous sugar formed by shearform processing in a non-aqueous sugar-nondissoluble liquid at a temperature wherein water is made available to said amorphous sugar at a rate and in an amount which provides substantially spheroidal polycrystallite structures.

2. The method of claim 1 wherein said structures are monodispersed.

3. The method of claim 1 wherein said shearform process comprises subjecting said feedstock to shear created by high speed spinning on a spinning head which casts material outwardly, said feedstock subjected to heating and shear in said head sufficient to create flash flow in said sugar carrier.

4. The method of claim 1 wherein said shearform process comprises heating said feedstock sufficiently to provide internal flow in said sugar carrier, ejecting said feedstock while said sugar has said internal flow condition, and subjecting said feedstock to disruptive fluid shear force to form multiple masses of carrier.

5. The method of claim 1 wherein said amorphous sugar further comprises an additive whereby said additive is co-crystallized in said substantially spheroidal polycrystallite structures.

6. The method of claim 5 wherein said additive is a material which can be integrated into said amorphous sugar without reducing the amorphism of said sugar and without deteriorating said substantially spheroidal polycrystallite structures.

7. The method of claim 6 wherein said additive is selected from the group consisting of flavorants, bio-affecting agents, dyes, fragrances, food products, food ingredients, and other compatible agents.

8. The method of claim 1 wherein said water further comprises an additive which co-crystallizes with said sugar to form said substantially spheroidal polycrystallite structures.

9. The method of claim 8 wherein said additive is selected from the group consisting of flavorants, bio-affecting agents, dyes, fragrances, food products, food ingredients, and other compatible agents.

10. The method of claim 9 wherein said additive is a bio-affecting agent selected from inhalants.

11. The method of claim 1 wherein said substantially spheroidal polycrystallite structures are microcrystalline.

12. The method of claim 11 wherein the mean diameter of said polycrystalline structures are not greater than about 50 μm.

13. The method of claim 1 wherein said non-aqueous sugar-nondissoluble liquid is maintained at a temperature of not less than about −20° C.

14. The method of claim 1 wherein said non-aqueous sugar-nondissoluble liquid and water form an azeotrope.

15. The method of claim 14 wherein said water and said sugar non-dissoluble liquid are combined in a azeotropic range.

16. The method of claim 14 wherein said non-aqueous sugar-nondissoluble liquid is ethanol.

17. The method of claim 1 wherein said water is present in an amount not greater than about 5% by weight.

18. The method of claim 16 wherein said water is present in an amount not greater than about 5.0% by weight.

19. The method of claim 1 wherein said feedstock further comprises a surfactant.

20. The method of claim 1 which further comprises disintegrating said spheroidal polycrystalline structures to form crystallites.

21. The method of 20 wherein said disintegrating comprises controllably adding an essentially sugar saturated aqueous liquid to said spheroidal polycrystalline structures.

22. The method of claim 20 wherein said crystallites are not greater than within monodispersibility of 5 μm.

23. A method of making a crystalline product comprising:
    controllably adding a solvent to an amorphous solid form of a solvent-soluble compound, said solvent soluble compound capable of forming crystals, said controlled addition conducted in the presence of a non-dissoluble liquid at a temperature and in an amount sufficient to form said crystalline product.

24. The method of claim 23 wherein said solvent is water.

* * * * *